United States Patent
Zhang et al.

(10) Patent No.: US 8,647,443 B2
(45) Date of Patent: *Feb. 11, 2014

(54) METHODS FOR CLEANING AN AUTOMATIC BIOCHEMICAL ANALYZER

(75) Inventors: Yuping Zhang, Shenzhen (CN); Mulong Liu, Shenzhen (CN); Wenjuan Xu, Shenzhen (CN); Jun Cheng, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 235 days.

This patent is subject to a terminal disclaimer.

(21) Appl. No.: 13/112,812

(22) Filed: May 20, 2011

(65) Prior Publication Data

US 2011/0224116 A1    Sep. 15, 2011

Related U.S. Application Data

(62) Division of application No. 12/255,455, filed on Oct. 21, 2008, now Pat. No. 8,003,586.

(30) Foreign Application Priority Data

Dec. 26, 2007  (CN) .......................... 2007 1 0305058

(51) Int. Cl.
  *B08B 7/04*   (2006.01)
  *B08B 9/00*   (2006.01)
  *B08B 3/00*   (2006.01)
  *C11D 3/20*   (2006.01)

(52) U.S. Cl.
  USPC ......... 134/22.13; 134/18; 134/22.14; 134/28; 134/29; 134/34; 510/161

(58) Field of Classification Search
  USPC ......... 134/18, 28, 29, 32, 34, 41, 42; 510/161
  See application file for complete search history.

(56) References Cited

U.S. PATENT DOCUMENTS

| | | |
|---|---|---|
| 4,683,008 A | 7/1987 | Betts |
| 6,342,474 B1 | 1/2002 | Kerobo et al. |
| 6,500,925 B1 | 12/2002 | Deisher et al. |
| 6,511,953 B1 | 1/2003 | Fontana et al. |
| 6,718,992 B1 | 4/2004 | Cardola et al. |
| 6,750,187 B2 | 6/2004 | Alam et al. |
| 2003/0119694 A1 | 6/2003 | Gladfelter et al. |
| 2004/0116317 A1* | 6/2004 | Burt et al. ..................... 510/447 |
| 2007/0238632 A1* | 10/2007 | Riesgo et al. ................. 510/386 |

FOREIGN PATENT DOCUMENTS

CN    1566304    1/2005

OTHER PUBLICATIONS

Huang, Wen-dong et al., "Study and Utilization of Detergent in Automatic Analyzer", China Academic Journal Electronic Publishing House, Mar. 2000, pp. 24-25, vol. 8, http://www.cnki.net.

* cited by examiner

*Primary Examiner* — Ling Choi
*Assistant Examiner* — Thuy-Ai Nguyen
(74) *Attorney, Agent, or Firm* — Kory D. Christensen; Matthew S. Bethards; Stoel Rives LLP

(57) ABSTRACT

A method of cleaning an automatic biochemical analyzer, wherein the cleaning solution includes: at least one anionic surfactant, at least one nonionic surfactant, an alkali metal hydroxide, an alkali metal citrate, and a buffering agent stabilizing the pH value above 13.0. In some embodiments, the cleaning solution provides low residual rate of proteins, low residual rate of lipids, desirable within-batch repeatability in clinical testing, low level of cross-contamination, and low level of reactant deposit after cleaning, without affecting test results of the biochemical analyzer. In some embodiments, the cleaning solution has no corrosive effects on the liquid path and reaction cup of the analyzer. The ingredients of the cleaning solution may also be biodegradable.

16 Claims, No Drawings

METHODS FOR CLEANING AN AUTOMATIC BIOCHEMICAL ANALYZER

CROSS-REFERENCE TO RELATED APPLICATIONS

This patent application is a divisional of now pending U.S. patent application Ser. No. 12/255,455, entitled "CLEANING SOLUTION FOR AN AUTOMATIC BIOCHEMICAL ANALYZER," filed on Oct. 21, 2008, which claims priority to Chinese Patent Application No. 200710305058.7, filed Dec. 26, 2007, for "A CLEANING SOLUTION FOR AUTOMATIC BIOCHEMICAL ANALYZER," the disclosures of which are fully incorporated herein by reference.

TECHNICAL FIELD

The present disclosure relates to a cleaning solution, in particular, a cleaning solution for automatic biochemical analyzer.

BRIEF SUMMARY

A cleaning solution for automatic biochemical analyzers is disclosed.

DETAILED DESCRIPTION

Automatic biochemical analyzers are frequently used in clinical practice. Clinical physicians often make their diagnosis according to the tests performed with the biochemical analyzer on the patient's body fluids for corresponding physiological indices, and therefore, the accuracy of these test results directly influences the diagnostic results. In a test procedure of the biochemical analyzer, a reaction cup is cleaned by a matched cleaning solution within a short period of time between two tests. The cleanliness of the reaction cup and the compatibility between the cleaning solution and the reaction cup often determine the accuracy of the subsequent test results. A desirable cleaning solution may have a desirable cleaning effect and a desirable compatibility with the reaction cup, such as being noncorrosive to the reaction cup. Therefore, the cleaning solution is of value for the daily maintenance of automatic biochemical analyzers as well as for the accuracy of the sample tests.

At present, manufacturers of automatic biochemical analyzers provide matched cleaning solutions specifically designed for the analyzer to meet the requirements of daily maintenance and to ensure test accuracy. Cleaning solutions are often different in that some include both acidic and basic solutions while others are solely basic, resulting in different cleaning effects. Most commercialized cleaning solutions designed for biochemical analyzers are basic cleaning solutions. Regardless of the type of cleaning solution used, it is desirable to have both a clinically acceptable cleaning effect and a desirable compatibility.

Currently, common cleaning solutions are divided into several types such as aqueous phase liquid and non-aqueous phase form. There are three primary aspects for common cleaning solutions. Those three aspects include:

1) Surfactants: Surfactants contained in cleaning solutions often comprise non-ionic surfactants, anionic surfactants, cationic surfactants or amphoteric surfactants. Different surfactants are selected to be used in different cleaning solutions according to the desired cleaning effects.

2) The formulation of cleaning solutions: Cleaning solutions for different applications are often different in their ingredients, such as the concentration of protease, enzyme stabilizer, bleach, colorant, foaming agent, antifoam, thickener and anticoagulant as well as pH value.

3) The desired application of cleaning solutions: Cleaning solutions are usually specifically designed for certain purposes, and thus the desired application is also a primary aspect of cleaning solutions.

Conventional cleaning solutions are usually directed to cleaning solutions for daily life uses such as cleaning solutions for dishwashers, laundry or the kitchen. There are only a few cleaning solutions for automatic biochemical analyzers. Particular application circumstances, such as proper washing temperature, the presence of a strong oxidant, extended washing time, or addition of washing enzyme, bleach and fluorescent agents are often required for conventional household cleaning solutions, making them incompatible for use with automatic biochemical analyzers. For example, conventional household cleaning solutions may cause damage to the analyzer, or it may make the index tested and thus the diagnosis inaccurate and potentially endanger the patient's life if these cleaning solutions are used in automatic biochemical analyzers. In addition, most cleaning solutions contain potential pollutants such as chlorine or phosphorus, which are considered undesirable to the environment and thus are prohibited in many nations.

With respect to the acidic or basic cleaning solutions currently provided by the manufacturers of a biochemical analyzer, they are specifically designed for their own biochemical analyzers and may be incompatible and even corrosive to the biochemical analyzers from a different manufacturer. The sequential use of acidic and basic cleaning solutions in a cleaning procedure lowers the residual rate of proteins and lipids, the level of cross-contamination and the level of reactant deposit, however, at the cost of test economy. On the other hand, if only an acidic or a basic cleaning solution is used for economic reasons, disadvantageous risks arise as some of the tested indices may be insufficient to the test requirement and may cause clinical misdiagnosis.

According to one embodiment of the present disclosure a non-corrosive, pollution-free and highly efficient cleaning solution for automatic biochemical analyzers is provided. One embodiment provides a cleaning solution for automatic biochemical analyzers comprising:

at least one anionic surfactant,
at least one nonionic surfactant,
an alkali metal hydroxide,
an alkali metal citrate, and
a buffering agent stabilizing the pH value above 13.0.

In some embodiments, the weight percentages of said ingredients in the cleaning solution are as follows:

| | |
|---|---|
| the anionic surfactant | 0.1-8%, |
| the nonionic surfactant | 0.01-15%, |
| the alkali metal hydroxide | 2-15%, |
| the alkali metal citrate | 1-10%, and |
| the buffer | 1-10%. |

In another embodiment, the weight percentages of said ingredients in the cleaning solution are as follows:

| | |
|---|---|
| the anionic surfactant | 0.1-5%, |
| the nonionic surfactant | 0.1-7.5%, |
| the alkali metal hydroxide | 4-13%, |

| | |
|---|---|
| the alkali metal citrate | 2-8%, and |
| the buffer | 1-10%. |

In some embodiments, said anionic surfactant is an alkyl sulfonate having a structure of formula (I):

$$R_1\text{—}SO_3X \quad (I),$$

wherein $R_1$ is an alkyl group having 12-18 carbon atoms, and X is an alkali metal ion.

In some embodiments, said anionic surfactant preferably is sodium dodecyl sulfonate (SDS) or $C_{12\text{-}16}H_{25\text{-}33}SO_3Na$(H-95).

In some embodiments, said nonionic surfactant is selected from at least one of: fatty alcohol polyoxyethylene ether, polyoxyethylene-polyoxypropylene-polyoxyethylene triblock copolymer, or fatty acid ester of polyoxyethylene sorbitan.

Furthermore, said fatty alcohol polyoxyethylene ether may have a structure of formula (II):

$$R_2\text{—}O\text{—}(C_2H_4O)_n\text{—}H \quad (II),$$

wherein $R_2$ is an alkyl group having 12~14 carbon atoms, and n is an integer between 2 and 20;

said polyoxyethylene-polyoxypropylene-polyoxyethylene triblock copolymer has a structure of formula (III):

$$(C_2H_4O)_a\text{—}(C_3H_6O)_b\text{—}(C_2H_4O)_c \quad (III),$$

wherein a and c are both integers and the sum of a and c is between 20 and 30, and b is an integer between 20 and 40; and said fatty acid ester of polyoxyethylene sorbitan has a structure of formula (IV):

$$C_{18}H_{34}O_6\text{—}(C_2H_4O)_m \quad (IV),$$

wherein m is 20, 40, 60 or 80.

Furthermore, said alkali metal hydroxide may be sodium hydroxide or potassium hydroxide.

In one embodiment, said alkali metal citrate is sodium citrate.

The cleaning solution for automatic biochemical analyzers comprises a combination of different non-ionic and anionic surfactants together with auxiliary alkali metal hydroxide, alkali metal citrate and a buffer system of proper pH. The cleaning solution may provide enhanced cleaning effects against organic materials such as lipids and proteins and inorganic ions, which address the problem that one single cleaning solution is insufficient to meet the clinical requirements when used in on-line automatic biochemical analyzer tests. Therefore, certain embodiments of the cleaning solution provide enhanced cleaning effects during the operation procedure of the biochemical analyzer and may lower the cost.

In one embodiment, during the test process, on-line cleaning with the cleaning solution disclosed, according to the pre-set cleaning program, can eliminate organic materials such as proteins and lipids and inorganic materials such as inorganic salts from the reaction cup, and therefore, subsequent tests will not be undesirably affected by preceding tests. Cleaning with the cleaning solution of one embodiment may also be characterized by low residual rate of proteins, low residual rate of lipids, desirable within-batch repeatability in clinical testing, low level of cross-contamination, and low level of reactant deposit after cleaning, without undesirably affecting the test results of the biochemical analyzer. Some embodiments of the cleaning solution are noncorrosive to the liquid path and reaction cup of the analyzer. Ingredients of the cleaning solution may be biologically degradable, thus minimizing contamination to the environment.

The present disclosure also relates to a basic cleaning solution for automatic biochemical analyzers. During the test procedure of automatic biochemical analyzers, in some embodiments, the cleaning system draws away the reaction mixture and the cleaning solution is injected to soak the reaction cup after the test is completed in the reaction cup. After the cleaning solution is drained from the reaction cup, the reaction cup may be purged with pure water to complete the cleaning process and is used for the next test.

Cleaning with some embodiments of the cleaning solution disclosed can eliminate the reaction mixture, organic materials such as proteins and lipids and inorganic materials such as inorganic salts remained or deposited in the reaction cup, as well as residual contaminants generated during a test. Consequently, this makes the consecutive test results within controllable ranges and provides reliable results for accurate clinical diagnosis. In some embodiments, the cleaning procedure has no corrosive effects on the liquid path and reaction cup of the analyzer, thus the tests are stable and fitting replacement rate is low. Meanwhile, certain embodiments of the cleaning solution disclosed make use of biodegradable materials; thus it may be pollution free and environmental-friendly. Furthermore, the requirements for cleaning may be satisfied by on-line cleaning with one single cleaning solution, therefore, sequential washing with acidic and basic cleaning solutions are dispensable, and the cost are thus lowered.

Certain embodiments of the cleaning solution comprise the following ingredients:

1) One or more anionic surfactants, which, in one embodiment are alkyl sulfonates having the structure:

$$R_1\text{—}SO_3X \quad (I),$$

wherein $R_1$ is an alkyl group having 12-18 carbon atoms, and X is an alkali metal ion. Exemplary surfactants are sodium dodecyl sulfonate (SDS), $C_{12\text{-}16}H_{25\text{-}33}SO_3Na$ (H-95) and the like.

The anionic surfactant in the cleaning solution serves mainly as wetting agent, emulsifier, dispersing agent and detergent, and is used to remove organic materials such as residual lipids in the reaction mixture. Meanwhile, the surfactant may be biodegradable, and thus is pollution-free.

In certain embodiments of the cleaning solution, the weight percentage of the alkyl sulfonate is generally between 0.1-8%, such as between 0.1-5%. Depending on the embodiment, a higher or lower percentage may make the cleaning inadequate.

2) One or more non-ionic surfactants. An exemplary non-ionic surfactant that can be used in the cleaning solution comprises substantially those from the following three subclasses:

(1) fatty alcohol polyoxyethylene ether, having a structure of formula (II)

$$R_2\text{—}O\text{—}(C_2H_4O)_n\text{—}H \quad (II)$$

wherein $R_2$ is an alkyl group having 12-14 carbon atoms and n is an integer between 2 and 20. A specific example is a condensate of fatty alcohol and nona-oxyethylene (AE0-9), which has the structure $C_{12\text{-}14}\text{—}O\text{—}(C_2H_4O)_9\text{—}H$;

(2) polyoxyethylene-polyoxypropylene-polyoxyethylene triblock copolymer, having a structure of formula (III)

$$(C_2H_4O)_a\text{—}(C_3H_6O)_b\text{—}(C_2H_4O)_c \quad (III),$$

wherein a and c are both integers and the sum of a and c is between 20 and 30, and b is an integer between 20 and 40. A specific example is $(C_2H_4O)_{13}$—$(C_3H_6O)_{30}$—$(C_2H_4O)_{13}$ (L-64); and (3) fatty acid ester of polyoxyethylene sorbitan, having a structure of formula (IV)

$$C_{18}H_{34}O_6\text{—}(C_2H_4O)_m \qquad (IV),$$

wherein m may be 20, 40, 60 or 80. A specific example is polyoxyethylene (20) sorbitan monolaurate of the structure $C_{18}H_{34}O_6(C_2H_4O)_{20}$ (Tween-20), or polyoxyethylene (80) sorbitan monooleate of the structure $C_{18}H_{34}O_6(C_2H_4O)_{80}$ (Tween-80).

The non-ionic surfactant in the cleaning solution serves mainly as an emulsifier, detergent, and wetting agent, and facilitates the removing of organic materials such as residual lipids, proteins and organic ions remaining in the reaction mixture. Meanwhile, such substances may be biodegradable and thus are pollution-free. In certain embodiments of the cleaning solution, the weight percentage of the non-ionic surfactant is between 0.01-15%, such as 0.1-7.5%. Depending on the embodiment, a higher or lower percentage may make the cleaning inadequate.

3) Alkali metal hydroxide. In certain embodiments, the alkali metal hydroxide can be sodium hydroxide or potassium hydroxide serving mainly to dissolve organic materials such as proteins and lipids and decrease the viscosity of the reaction mixture, thus increasing the cleaning efficiency.

In certain embodiments of the cleaning solution, the weight percentage of the alkali metal hydroxide is generally between 2-15%, such as between 4-13%. In some embodiments, a lower percentage may be less effective for dissolving organic materials such as proteins and lipids and lowering the viscosity of the reaction mixture.

4) Alkali metal citrate. In certain embodiments, the alkali metal citrate is sodium citrate which serves mainly as a solubilizer for enhancing the solubility of inorganic and/or organic ions in the solution to increase the cleaning efficiency.

In certain embodiments of the cleaning solution, the weight percentage of the alkali metal citrate is generally between 1-10%, such as 2-8%. In some embodiments, a lower percentage may be less effective for dissolving organic materials such as proteins and lipids and lowering the viscosity of the reaction mixture, thus making the cleaning inadequate.

5) A buffer system for stabilizing pH value.

In certain embodiments of the cleaning solution, the buffer is mainly used to stabilize the pH value of the solution above 13.0. There is no specific limitation on the composition of the buffer system used. The buffer can include organic acids (or salts), inorganic acids (or salts), or a mixture thereof. Specific examples are 2-amino-2-hydroxymethyl-1,3-propylene glycol, tris, citric acid, citrate buffer, etc. In addition to stabilizing pH value, the buffer system can also increase the solubility of inorganic ions, and thus further enhance the cleaning efficiency against inorganic ions. A suitable weight percentage of the buffer is generally within the range of between 1-10% in some embodiments.

The cleaning solution disclosed for automatic biochemical analyzers may comprise a combination of different non-ionic and anionic surfactants together with auxiliary alkali metal hydroxide, alkali metal citrate and a suitable buffer system. The cleaning solution provides enhanced cleaning effects against organic materials such as lipids and proteins and inorganic ions. In certain embodiments, this addresses the problem with conventional cleaners that one single cleaning solution is insufficient to meet the clinical requirements when used in the on-line automatic biochemical analyzer tests as well as the problem that sequential use of both acidic cleaning solution and basic cleaning solution is needed in a thorough cleaning to meet the clinical requirements. Therefore, the cleaning solution disclosed provides enhanced cleaning effects during the operation procedure of the biochemical analyzer and may lower the cost.

The present disclosure is further illustrated in details with reference to the following examples.

Example 1

Using water as the solvent, a basic cleaning solution for automatic biochemical analyzers was prepared according to the following weight percentages:

| | |
|---|---|
| Tris | 0.4%; |
| H-95 | 2.5%; |
| AEO-9 | 2.0%; |
| L-64 | 2.0%; |
| Tween-20 | 1.0%; |
| Sodium citrate | 2.0%; |
| Citric acid | 2.0%; and |
| KOH (45%) | 10.0%; | wherein the KOH (45%) comprises 10.0% of the formulation as a whole. The cleaning solution formulated in accordance with the above proportion had a pH value of 13.6.

The online cleaning efficiency of the above basic cleaning solution was tested with Mindray BS-400 automatic biochemical analyzer for residual rate of proteins, residual rate of lipids, deposit of reactants, within-batch repeatability in clinical testing, cross-contamination (especially the triglyceride reactants cross-contamination in lipase test), alteration to the surface condition of the reaction cup, shape transformation of the reaction cup, etc.

The indices tested were within the controllable range of the test, namely: the residual rates of proteins and lipids were both below the order of magnitude of $10^{-4}$, which would not affect later tests; no deposit of reactants was observed; within-batch repeatability in clinical testing was acceptable, with a coefficient of variation of test results from the same sample below 3%; no cross-contamination was observed, especially no triglyceride reactants cross-contamination was observed in a lipase test; in the testing of alteration to the surface condition of the reaction cup with potassium dichromate dye liquor, the coefficient of variation of the dye liquor precision was below 1%; and no shape transformation of the reaction cup was observed.

In addition, the cleaning solution provided a desirable cleaning effect and compatibility, and was observed to be noncorrosive to the liquor paths of the system. Furthermore, only one cleaning solution was used in the cleaning procedure so that the clinical test cost was lowered.

Example 2

Using water as the solvent, a basic cleaning solution for automatic biochemical analyzers was prepared according to the following weight percentages:

| | |
|---|---|
| Tris | 0.4%; |
| H-95 | 0.6%; |
| SDS | 2.0%; |
| AEO-9 | 1.5%; |

|   |   |
|---|---|
| L-64 | 1.5%; |
| Sodium citrate | 4.0%; |
| Citric acid | 4.0%; and |
| KOH (45%) | 12.0%. |

The cleaning solution formulated in accordance with the above proportion had a pH value of 13.6.

The online cleaning efficiency of the above basic cleaning solution was tested with Mindray BS-400 automatic biochemical analyzer for residual rate of proteins, residual rate of lipids, deposit of reactants, within-batch repeatability in clinical testing, cross-contamination (especially the triglyceride reactants cross-contamination in lipase test), alteration to the surface condition of the reaction cup, shape transformation of the reaction cup, etc.

The indices tested were within the controllable range of the test, namely: the residual rates of proteins and lipids were both below the order of magnitude of $10^{-4}$, which would not affect later tests; no deposit of reactants was observed; within-batch repeatability in clinical testing was acceptable, with a coefficient of variation of test results from the same sample below 3%; no cross-contamination was observed, especially no triglyceride reactants cross-contamination was observed in a lipase test; in the testing of alteration to the surface condition of the reaction cup with potassium dichromate dye liquor, the coefficient of variation of the dye liquor precision was below 1%; and no shape transformation of the reaction cup was observed.

In addition, the cleaning solution provided a desirable cleaning effect and compatibility, and was observed to be noncorrosive to the liquor paths of the system. Furthermore, only one cleaning solution was used in the cleaning procedure so that the clinical test cost was lowered.

Example 3

Using water as the solvent, a basic cleaning solution for automatic biochemical analyzers was prepared according to the following weight percentages:

|   |   |
|---|---|
| Tris | 0.4%; |
| H-95 | 1.0%; |
| SDS | 2.0%; |
| AEO-9 | 1.5%; |
| L-64 | 1.5%; |
| Tween-20 | 0.5%; |
| Sodium citrate | 4.0%; |
| Citric acid | 4.0%; and |
| KOH (45%) | 12.0% |

The cleaning solution formulated in accordance with the above proportion had a pH value of 13.6.

The online cleaning efficiency of the above basic cleaning solution was tested with Mindray BS-400 automatic biochemical analyzer for residual rate of proteins, residual rate of lipids, deposit of reactants, within-batch repeatability in clinical testing, cross-contamination (especially the triglyceride reactants cross-contamination in lipase test), alteration to the surface condition of the reaction cup, shape transformation of the reaction cup, etc.

The indices tested were within the controllable range of the test, namely: the residual rates of proteins and lipids were both below the order of magnitude of $10^{-4}$, which would not affect later tests; no deposit of reactants was observed; within-batch repeatability in clinical testing was acceptable, with a coefficient of variation of test results from the same sample below 3%; no cross-contamination was observed, especially no triglyceride reactants cross-contamination was observed in a lipase test; in the testing of alteration to the surface condition of the reaction cup with potassium dichromate dye liquor, the coefficient of variation of the dye liquor precision was below 1%; and no shape transformation of the reaction cup was observed.

In addition, the cleaning solution provided a desirable cleaning effect and compatibility, and was observed to be noncorrosive to the liquor paths of the system. Furthermore, only one cleaning solution was used in the cleaning procedure so that the clinical test cost was lowered.

Example 4

Using water as the solvent, a basic cleaning solution for automatic biochemical analyzers was prepared according to the following weight percentages:

|   |   |
|---|---|
| Tris | 0.4%; |
| H-95 | 1.0%; |
| SDS | 2.0%; |
| AEO-9 | 3.5%; |
| Sodium citrate | 4.0%; |
| Citric acid | 4.0%; and |
| KOH (45%) | 12.0%. |

The cleaning solution formulated in accordance with the above proportion had a pH value of 13.6.

The online cleaning efficiency of the above basic cleaning solution was tested with Mindray BS-400 automatic biochemical analyzer for residual rate of proteins, residual rate of lipids, deposit of reactants, within-batch repeatability in clinical testing, cross-contamination (especially the triglyceride reactants cross-contamination in lipase test), alteration to the surface condition of the reaction cup, shape transformation of the reaction cup, etc.

The indices tested were within the controllable range of the test, namely: the residual rates of proteins and lipids were both below the order of magnitude of $10^{-4}$, which would not affect later tests; no deposit of reactants was observed; within-batch repeatability in clinical testing was acceptable, with a coefficient of variation of test results from the same sample below 3%; no cross-contamination was observed, especially no triglyceride reactants cross-contamination was observed in a lipase test; in the testing of alteration to the surface condition of the reaction cup with potassium dichromate dye liquor, the coefficient of variation of the dye liquor precision was below 1%; and no shape transformation of the reaction cup was observed.

In addition, the cleaning solution provided a desirable cleaning effect and compatibility, and was observed to be noncorrosive to the liquor paths of the system. Furthermore, only one cleaning solution was used in the cleaning procedure so that the clinical test cost was lowered.

While the present disclosure is further described in detail with reference to specific embodiments, the invention, as claimed, should not be construed to be limited thereto. It is apparent to those skilled in the art that various modifications and alteration can be made without departing from the spirit and scope of the inventive concept and therefore are within the scope of the claimed invention.

What is claimed is:

1. A method of cleaning an automatic biochemical analyzer, comprising:

obtaining a cleaning solution configured to be compatible for use with a biochemical analyzer, the cleaning solution comprising:

at least one anionic surfactant present in a weight percentage of between 0.1 to 8.0%, the anionic surfactant comprising an alkyl sulfonate having a structure of formula (I):

$$R_1\text{—}SO_3X \qquad (I),$$

wherein $R_1$ is an alkyl group having between 12 to 18 carbon atoms, and X is an alkali metal ion;

at least one nonionic surfactant present in a weight percentage of between 0.01 to 15.0%;

an alkali metal hydroxide present in a weight percentage of between 2.0 to 15.0%;

an alkali metal citrate present in a weight percentage of between 1.0 to 10.0%; and a buffering agent stabilizing the pH value above 13.0, the buffering agent present in a weight percentage of between 1.0 to 10.0%; and applying the cleaning solution to the automatic biochemical analyzer.

2. The method of claim 1, wherein applying the cleaning solution comprises applying an amount of the cleaning solution sufficient to eliminate proteins, lipids and inorganic salts from a reaction cup of the automatic biochemical analyzer.

3. The method of dam 2, wherein applying the cleaning solution sufficient to eliminate proteins, lipids and inorganic salts comprises applying an amount of cleaning solution sufficient such that tests subsequent to cleaning the automatic biochemical analyzer are not affected by tests preceding the cleaning of the automatic biochemical analyzer.

4. The method of claim 2, wherein applying the cleaning solution sufficient to eliminate proteins, lipids and inorganic salts comprises applying an amount of cleaning solution sufficient to obtain a residual rate of proteins and lipids below an order of magnitude of $10^{-4}$ after cleaning.

5. The method of claim 1, wherein obtaining the cleaning solution comprises obtaining a cleaning solution which is non-corrosive to a reaction cup used with the automatic biochemical analyzer.

6. The method of claim 1, wherein obtaining the cleaning solution comprises obtaining a cleaning solution where the anionic surfactant is present in a weight percentage of between 0.1-5%; the nonionic surfactant is present in a weight percentage of between 0.1-7.5%; the alkali metal hydroxide is present in a weight percentage of between 4-13%; the alkali metal citrate is present in a weight percentage of between 2-8%, and the buffer is present in a weight percentage of between 1-10%.

7. The method of claim 1, wherein obtaining the cleaning solution comprises obtaining a cleaning solution where the alkyl sulfonate is sodium dodecyl sulfonate or $C_{12-16}H_{25-33}SO_3Na$.

8. The method of claim 1, wherein obtaining the cleaning solution comprises obtaining a cleaning solution with a nonionic surfactant selected from at least one of: fatty alcohol polyoxyethylene ether, polyoxyethylene-polyoxypropylene-polyoxyethylene triblock copolymer, or fatty acid ester of polyoxyethylene sorbitan.

9. The method of claim 8, wherein the nonionic surfactant is a fatty alcohol polyoxyethylene ether having a structure of formula (II):

$$R_2\text{—}O\text{—}(C_2H_4O)_n\text{—}H \qquad (II),$$

wherein $R_2$ is an alkyl group having between 12-14 carbon atoms, and n is an integer between 2 and 20.

10. The method of claim 9, wherein n is 9.

11. The method of claim 8, wherein the nonionic surfactant is a polyoxyethylene-polyoxypropylene-polyoxyethylene triblock copolymer having a structure of formula (III):

$$(C_2H_4O)_a\text{—}(C_3H_6O)_b\text{—}(C_2H_4O)_c \qquad (III),$$

wherein a and c are both integers and the sum of a and c is between 20 and 30, and b is an integer between 20 and 40.

12. The method of claim 11, wherein a is 13, b is 30 and c is 13.

13. The method of claim 8, wherein the nonionic surfactant is a fatty acid ester of polyoxyethylene sorbitan having a structure of formula (IV):

$$C_{18}H_{34}O_6\text{—}(C_2H_4O)_m \qquad (IV),$$

wherein m is 20, 40, 60 or 80.

14. The method of claim 13, wherein m is 20 or 80.

15. The method of claim 1, wherein obtaining the cleaning solution comprises obtaining a cleaning solution wherein the alkali metal hydroxide comprises sodium hydroxide or potassium hydroxide.

16. The method of claim 1, wherein obtaining the cleaning solution comprises obtaining a cleaning solution wherein the alkali metal citrate comprises sodium citrate.

* * * * *